United States Patent [19]
Vickers

[11] Patent Number: 5,385,932
[45] Date of Patent: Jan. 31, 1995

[54] HMG-COA REDUCTASE INHIBITOR METABOLITES

[75] Inventor: Stanley Vickers, Perkasie, Pa.

[73] Assignee: Merck & Co., Inc., Rahway, N.J.

[21] Appl. No.: 834,948

[22] Filed: Feb. 18, 1992

Related U.S. Application Data

[62] Division of Ser. No. 577,184, Sep. 4, 1990, Pat. No. 5,112,857.

[51] Int. Cl.$^6$ .............................................. A61K 31/365
[52] U.S. Cl. ...................................... 514/460; 549/292
[58] Field of Search ......................... 549/292; 514/460

[56]  References Cited
U.S. PATENT DOCUMENTS

| 4,517,373 | 5/1985 | Terahara et al. | 549/292 |
| 4,537,859 | 8/1985 | Terahara et al. | 435/146 |
| 4,584,389 | 4/1986 | Sletzinger et al. | 549/292 |
| 4,604,472 | 8/1986 | Ide et al. | 549/292 |
| 4,733,003 | 3/1988 | Ide et al. | 560/119 |
| 4,833,258 | 5/1989 | Smith et al. | 549/292 |
| 4,897,402 | 1/1990 | Duggan et al. | 514/312 |
| 4,921,974 | 5/1990 | Duggan et al. | 549/214 |
| 4,940,727 | 7/1990 | Inamine et al. | 514/450 |
| 4,963,538 | 10/1990 | Duggan et al. | 514/99 |
| 5,073,568 | 12/1991 | Wovkulich et al. | 514/460 |
| 5,173,487 | 12/1992 | Saunders et al. | 549/292 |

FOREIGN PATENT DOCUMENTS

| 0325817 | 8/1989 | European Pat. Off. . |
| 0331240 | 9/1989 | European Pat. Off. . |
| 0369288 | 5/1990 | European Pat. Off. . |
| 57-185275 | 11/1982 | Japan . |
| 58-210043 | 12/1983 | Japan . |
| 60-97973 | 5/1985 | Japan . |
| 62-277377 | 12/1987 | Japan . |
| 2075013 | 11/1981 | United Kingdom . |

OTHER PUBLICATIONS

Terahara et al. "MB 530B Derivatives and their Pharmaceutical Compositions" CA 99: 70288t (1983).

*Primary Examiner*—C. Warren Ivy
*Assistant Examiner*—A. A. Owens
*Attorney, Agent, or Firm*—Catherine A. Dolan; Melvin Winokur; Paul D. Matukaitis

[57]  ABSTRACT

This invention relates to compounds of formulae I and II which are metabolites of tetrahydrosimvastatin and 5-hydroxy-tetrahydrosimvastatin and which are HMG—CoA reductase inhibitors.

5 Claims, No Drawings

HMG-COA REDUCTASE INHIBITOR METABOLITES

This is a division of application Ser. No. 07/577,184, filed Sep. 4, 1990 now U.S. Pat. No. 5,112,857.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihypercholesterolemic agents that function by limiting cholesterol biosynthesis by inhibiting the enzyme, HMG—CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

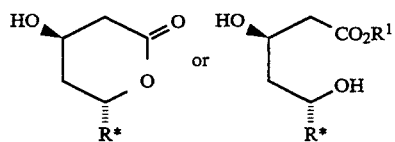

wherein:
$R^1$ is hydrogen, $C_{1-5}$ alkyl or $C_{1-5}$ alkyl substituted with a member of the group consisting of phenyl, dimethylamino, or acetylamino; and
$R^*$ is a polyhydronaphthyl moiety.

U.S. Pat. No. 4,517,373 discloses semi-synthetic hydroxy containing compounds represented by the above general formula wherein $R^*$ is

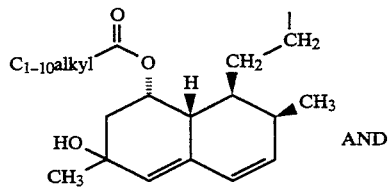

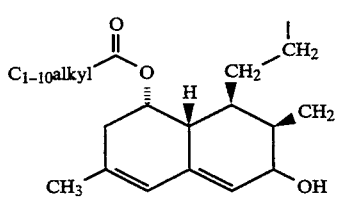

U.S. Pat. No. 4,537,859 and U.S. Pat. No. 4,448,979 also disclose semi-synthetic hydroxy-containing compounds represented by the above general formula wherein $R^*$ is

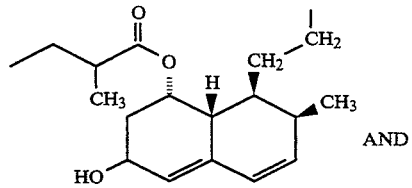

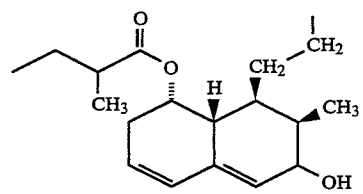

These compounds are prepared by the action of certain microorganisms on the corresponding non-hydroxylated substrates. One such organism described in U.S. Pat. No. 4,537,859 is of the genus Nocardia.

U.K. Patent 2,075,013 discloses semi-synthetic hydroxy containing compounds represented by the above general formula wherein $R^*$ is:

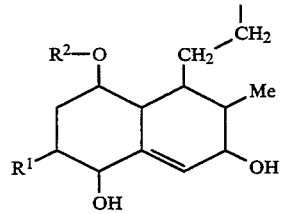

wherein $R^1$ is H or Me, and $R^2$ is H or acyl.

U.S. patent application Ser. No. 254,525 filed Oct. 6, 1988 discloses 6-substituted compounds of the above general formula wherein $R^*$ is:

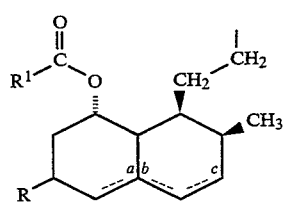

wherein R is

and $R^1$, $R^4$, $R^7$, $R^8$ and $R^9$ are broadly defined organic moieties.

U.S. Pat. Nos. 4,604,472 and 4,733,003 disclose compounds of the above formula wherein $R^*$ is:

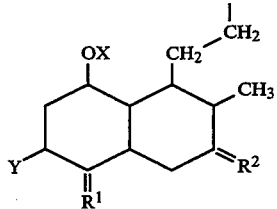

wherein X represents a hydrogen atom or a 2-methylbutyryl group, Y represents a hydrogen atom or a methyl group and $R^1$ and $R^2$ are the same or different and each represents an oxygen atom or a group of formula =N—$OR^3$ where $R^3$ is a hydrogen or alkyl moiety.

Copending U.S. patent application Ser. No. 213,010 filed Jun. 29, 1988 discloses 5-oxygenated compounds of the above general formula wherein R* is

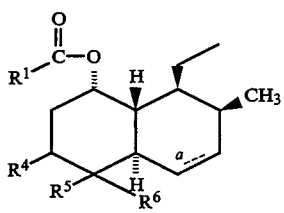

$R^4$ is H, alkyl or substituted alkyl and $R^5$ and $R^6$ are H, OH or $OR^7$ where $R^7$ represents a phosphoryl or acyl moiety.

Copending U.S. patent application Ser. No. 212,767 filed Jun. 29, 1988 discloses 5-Oxa, Thia and Aza compounds of the above general formula where R* is:

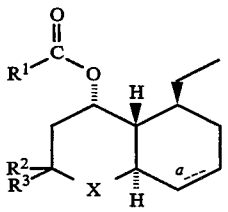

$R^1$ is an alkyl or substituted alkyl group, $R^2$ and $R^3$ are H, alkyl or substituted alkyl and X is O, $S(O)_n$ or $NR^4$ where $R^4$ is H, alkyl or substituted alkyl.

DETAILED DESCRIPTION OF THE INVENTION

This invention relates to HMG—CoA reductase inhibitors of formulae (I) and (II):

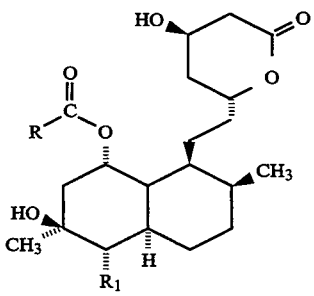

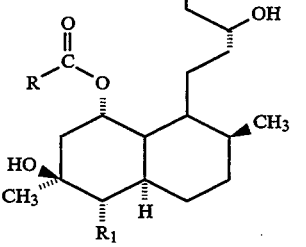

wherein:
R is $C_{1-10}$alkyl;
$R_1$ is H or O—$R_2$;
$R_2$ is H or $C_{1-5}$alkyl; and
$R_3$ is H or $C_{1-5}$alkyl or a pharmaceutically acceptable salt of a compound of formula (II) wherein $R_3$ is H,
In one embodiment of this invention
R is 2-butyl or 2-methyl-2-butyl-
$R_1$ is H or $OR_2$,
Specifically exemplifying this embodiment are those compounds wherein:
(a) R is 2-methyl-2-butyl and $R_1$ is H;
(b) R is 2-methyl-2-butyl and $R_1$ is OH;
(c) R is 2-butyl and $R_1$ is H;
(d) R is 2-butyl and $R_1$ is OH, The instant compounds are formed as rat liver metabolites from tetrahydrosimvastatin and its 8-ester analogs and from 5-hydroxy or 5-alkoxytetrahydrosimvastatin and its 8-ester analogs. The preparation of these starting materials is disclosed in U.S. Pat. Nos. 4,444,784 and 4,864,035 and EPO publication 349,063.

The compounds of the formula (II) wherein $R_3$ is hydrogen or a pharmaceutically acceptable salt thereof are readily prepared by the mild basic hydrolysis of the lactone moiety of the compounds of formula (I) followed by careful acidification and formation of the appropriate salt utilizing standard procedures.

Preferred metal salts of the compounds of the present invention are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, a, β-diaminobutyric acid or ornithine.

Preferred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl, or pentyl esters, of which the methyl ester is preferred. However, other esters such as phenyl-$C_{1-5}$alkyl may be employed if desired.

Metal salts of the carboxylic acids of formula (II) may be obtained by contacting a hydroxide, carbonate or similar solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example, a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the alcohol itself, benzene, chloroform, ethers and the like. Alternatively, the desire product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

After alkaline hydrolysis of the lactone ring the intrinsic HMG—CoA reductase inhibition activity was measured in an vitro protocol based on a method published in Proc. Natl. Acad. Sci. U.S.A. 77, 3957–3961 (1980).

The $IC_{50}$ value of the test compound was compared with that of its parent determined simultaneously. For estimation of relative inhibitory potencies, lovastatin (in the form of its hydroxy acid) was assigned a value of 100.

Representative of the intrinsic HMG—CoA reductase inhibitory activities of the claimed compounds are the following relative potencies for compounds of formula (I).

| Compound | Potency (Relative to Lovastatin = 100) |
|---|---|
| 6(R)-[2-[8(S)-(2,2-dimethylbutyryloxy)-2(S)-methyl-5(S),6(S)-dihydroxy-6(S)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one | 40 |
| 6(R)-[2-[8(S)-(2,2-dimethylbutyryloxy)-2(S),6(R)-dimethyl-6(R)-hydroxy-1,2,3,4a(R),5,6,7,8,8a(R)-decahydronaphthyl-1(S)]ethyl]-4(R)-hydroxy-3,4,5,6-tetrahydro-2H-pyran-2-one | 2 |

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims approved hereto.

EXAMPLE 1

Preparation of 6(R)-[2-[8(S)-(2,2-dimethylbutyryloxy)-2(S)-methyl-5(S),6(S)-dihydroxy-6(S)-methyl-1,2,3,4, 4a (R),5,6,7,8,8a (R)-decahydronaphthyl-1(S)]ethyl]-4(R)-hydroxy-3,4,5,6-tetrahydro-2H-pyran-2-one a) Microsomal Preparation Rat liver tissue (55.6 g) was homogenized in 0.05M Tris −1.15% KCl buffer at pH 7.5 (100 ml). The homogenates were centrifuged at 10,000 RPM for 20 '. The supernatants were filtered through glass wool and then centrifuged as 100,000 g for 90'. After the supernatant was discarded the pellet was suspended in 10 mM EDTA −1.15% KCl (100 ml) and recentrifuged at 100,000 g for 90 minutes. The supernatant was discarded and the pellet was resuspended in 0.25M sucrose (15 ml). Microsomes were stored at −80° under $N_2$. Protein concentration (as determined by Biuret reaction) was 40 mg/ml of final suspension.

b) Incubation of [$^{14}$C] 6(R)-[2-[8(S)-(2,2-dimethylbutyryloxy)-2(S)-methyl-5(R)-hydroxy-6(S)-methyl-1,2, 3,4,4a(R),5,6,7,8,8a(R)-decahydronaphthyl-1(S)]ethyl]-4(R)-hydroxy-3,4,5,6,-tetrahydro-2H-pyran-2-one and microsomes

[$^{14}$C] 6(R)-[2-[8(S)-(2,2-dimethylbutyryloxy)-2(S)-methyl-5(R)-hydroxy-6(S)-methyl-1,2,3,4, 4a(R),5,6,7,8,8a(R)-decahydronaphthyl-1(S)]ethyl]-4(R)-hydroxy-3,4,5,6,-tetrahydro-2H-pyran-2-one (compound A)(40 μg) in 20 λ of DMSO was placed in a tube with rat liver microsomes (1 mg in 100 μl of broth) Mg Cl$_2$ (30 μl of a 0.1M solution), NADPH (50 μl of a 0.01M solution) and phosphate buffer (100 λ of a.1M solution, pH 7.4).

Twenty five such tubes were incubated at 37° in a water bath, for 30 minutes. Acetone (1 ml) was added to each tube, followed by ethyl acetate (5 ml). The ethyl acetate was evaporated and the residue was reconstituted in methanol and fractionated by HPLC.

The components that were used for HPLC included a Perkin-Elmer Model Series 410 pump, and an ISS-100 autosampler or a Bioanalytical pump and a WISP autosampler. Samples were injected on to an E. Merck Lichrosorb RP-18 (5 μm) analytical column and subjected to gradient elution with 5 mMHCOOH and acetonitrile. The proportion of the latter was linearly increased from 15% to 75% in 30 min. The flow rate of the mobile phase was 2 ml/min. Ether a Foxy or a Gilson model fraction collector was used to collect eluate.

The label in the microsomal incubation was extracted into ethyl acetate. HPLC analysis indicated that most of the label represented unchanged starting material "A" (52%) and a major metabolite (23%). Both unchanged starting material "A" and the metabolite were isolated. Preliminary work indicated that the metabolite was susceptible to alkaline hydrolysis. It was concluded that the metabolite was a lactone. Mass spectral (fast atom bombardment) analysis showed that the molecular weight of the metabolite was 454 (M+Na=477). As expected the molecular weight of the recovered "A" was 438 (M+Na=461). NMR structure determinations confirmed the structure of the recovered "A" and also showed that the metabolite was a stereoselectively hydroxylated derivative of "A". The metabolite was identified as 6(R)-[2-[8 (S)-(2,2-dimethylbutyryloxy)-2(S)-methyl-5(S),6(R)-dihydroxy-6(R)-methyl-1,2,3,4,4a(R),5,6,7,8,8a (R)-decahydronaphthyl-1(S)]ethyl]-4(R)-hydroxy-3,4,5,6-tetrahydro-2H-pyran-2-one.

$^1$H NMR (CD$_3$CN) δ5.07(1H), 4.47(1H), 4.19(1H), 3.20(1H), 3.10(1H), 2.79(1H), 2.64(1H), 2.59(1H), 2.42(1H),1.98(1H), 1.82(1H), 1.74(1H), 1.64(1H), 1.61(1H), 1.57(1H), 1.42(1H), 1.37(1H), 1.25(1H), 1.16(3H), 1.15(3H), 1.14(3H), 0.835(1H), 0.82(1H).

EXAMPLE 2

Preparation of 6(R)-[2-[8(S)-(2,2-dimethylbutyryloxy)-2(S),6(R)-dimethyl-6(R)-hydroxy-1,2,3,4,4a (R),5,6,7,8,8a (R)-decahydronaphthyl-1(S)]ethyl]-4(R)-hydroxy-3, 4,5,6-tetrahydro-2H-pyran-2-one

[$^{14}$C] 6(R)-[2-[8(S)-(2,2-dimethylbutyryloxy)-2(S),6(R)-dimethyl-1,2,3,4,4a(R),5,6,7,8, 8a(R)-decahydronaphthyl-1(S)]ethyl]-4(R)-hydroxy-3,4,5,6-tetrahydro-2H-pyran-2-one (compound B) 1 mg in 0.5 ml of acetone was placed in a conical flask with rat liver microsomes (25 mg in 2.5 ml of broth) MgCl$_2$ (0.75 ml of a 0.5M solution), NADPH (1.25 ml of a 0.01M solution/and phosphate buffer (2.5 ml of a 1M solution, pH 7.4.

The flask was incubated at 37° in a water bath for 60 minutes. Acetone (2 ml) was then added. The contents of the flask were sequentially extracted with methyl-t.butyl ethyl ether (250 ml) and ethyl acetate (250 ml). Both extracts were dried over sodium sulfate and then concentrated and reconstituted in methanol. The methanolic solution from the methyl-t.butyl ethyl ether extract was fractionated by HPLC. Samples were injected onto an BrownLee RP 8 Spheri 5 analytical column (4.6×100 mm) and subjected to gradient elution with 5 mM HCOOH and acetonitrile. The proportion of the latter was linearly increased from 30% to 90% in 30 min. The flow rate of the mobile phase was 1 ml/min. A Foxy model fraction collector was used to collect eluate.

Most of the label in the extract was unchanged "B" (66%) and a major metabolite (34%). Mass spectral (fast atom bombardment) analysis showed that the molecular weight of the metabolite was 438 (M+Na=461). As expected the molecular weight of the recovered "B" was 422 (M+H=423, M+Na=445). NMR structure determinations showed that the metabolite was hydroxylated at the 6-position of the polyhydronaphthyl ring.

$^1$H NMR (CD$_3$CN) δ5.26(1H), 4.56(1H), 4.37(1H), 2.737(1H), 2.60(1H), 2.05(1H), 1.33(3H), 1.17(3H), 1.16(3H), 0.85(5H), 0.82(6H).

EXAMPLE 3

Preparation of Ammonium Salts of Compounds II

The lactone (1.0 mmol) from Example 1 is dissolved with stirring in 0.1N NaOH (1.1 mmol) at ther and the extract washed with brine and dried (MgSO$_4$). The MgSO$_4$ is removed by filtration and the filtrate saturated with ammonia (gas) to give the ammonium salt.

EXAMPLE 4

Preparation of Alkali and Alkaline Earth Salts of Compounds II

To a solution of 44 mg of lactone from Example 1 in 2 ml of ethanol is added 1 ml of aqueous 0.1N NaOH. After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 5

Preparation of Ethylenediamine Salts of Compounds II

To solution of 0.50 g of the ammonium salt from Example 3 in 10 ml of methanol is added 0.04 ml of ethylenediamine. The methanol is stripped off under vacuum to obtain the desired ethylenediamine salt.

EXAMPLE 6

Preparation of Tris(hydroxymethyl)aminomethane Salts of Compounds II

To a solution of 202 mg of the ammonium salt from Example 3 in 5 ml of methanol is added a solution of 50 mg of tris(hydroxymethyl)aminomethane is 5 ml of methanol. The solvent is removed in vacuo to afford the desired tris(hydroxymethyl)aminomethane salt.

EXAMPLE 7

Preparation of L-Lysine Salts of Compounds II

A solution of 0.001 mole of L-lysine and 0.0011 mole of the ammonium salt from Example 3 in 15 ml of 85% ethanol is concentrated to dryness in vacuo to give the desired L-lysine salt.

Similarly prepared are the L-arginine, L-ornithine, and N-methyglucamine salts.

EXAMPLE 8

Preparation of Tetramethylammonium Salts of Compounds II

A mixture of 68 mg of ammonium salt from Example 3 in 2 ml of methylene chloride and 0.08 ml of 24% tetramethylammonium hydroxide in methanol is diluted with ether to yield the desired tetramethylammonium salt.

EXAMPLE 9

Preparation of Methyl Esters of Compounds II

To a solution of 400 mg of lactone from Example 1 in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of the alkoxides derived from propanol, butanol, isobutanol, t-butanol, amyl alcohol, isoamyl alcohol, 2-dimethylaminoethanol, benzyl alcohol, phenethanolm 2-acetamidoethanol and the like, and employing the corresponding alchohol, phenethanol, 2-acetamidoethanol and the like, and employing the corresponding alcohol as solvent, the corresponding esters are obtained.

EXAMPLE 10

Preparation of Free Dihydroxy Acids

The sodium salt of the compound II from Example 4 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding parent lactone on standing at room temperature. The dihydroxy acid form can be maintained by increasing the pH above 7.0.

EXAMPLE 11

As a specific embodiment of a composition of this invention, 20 mg of lactone from Example 1 is formulated with sufficient finely divided lactose to provide a total amount of 580 to 590 mg to fill a size 0, hard-gelatin capsule.

What is claimed is:

1. A compound of structural formula (I) or (II):

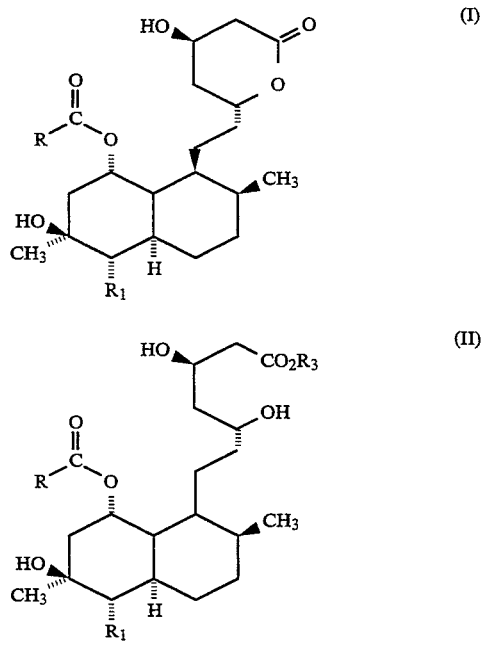

wherein:

R is $C_{1-10}$alkyl;

$R_1$ is H; and $R_3$ is H or $C_{1-5}$alkyl or a pharmaceutically acceptable salt of a compound of formula (II) wherein $R_3$ is H, 2. The compound of claim 1 wherein R is 2-butyl or 2-methyl-2-butyl; and $R_1$ is H.

3. The compound of claim 2 selected from the group wherein $R_3$ is H and wherein:

(a) R is 2-methyl-2-butyl and $R_1$ is H:

(b) R is 2-butyl and $R_1$ is H;

or a pharmaceutically acceptable salt thereof.

4. A hypocholesterolemic, hypolipidemic pharmaceutical composition comprising a pharmaceutically acceptable carrier and a therapeutically effective amount of a compound as defined in claim 1.

5. A method of inhibiting cholesterol biosynthesis in a subject in need of such treatment which comprises the administration of an antihypercholesterolemic effective amount of a compound of claim 1.

* * * * *